United States Patent
Anderson et al.

(10) Patent No.: US 7,932,050 B2
(45) Date of Patent: Apr. 26, 2011

(54) ENZYMATIC SUBSTRATES DERIVED FROM PHENOXAZINONE AND THEIR USE AS DEVELOPERS IN DETECTION OF MICROORGANISMS WITH PEPTIDASE ACTIVITY

(75) Inventors: Rosaleen Joy Anderson, Gateshead (GB); Paul William Groundwater, Sunderland (GB); Arthur James, Cockermouth (GB); Daniel Monget, Saint-Sorlin-en-Bugey (FR); Andrey Victorovich Zaytsev, Newcastle upon Tyne (GB)

(73) Assignee: bioMerieux, Marcy L'Etoile (FR)

( * ) Notice: Subject to any disclaimer, the term of this patent is extended or adjusted under 35 U.S.C. 154(b) by 2 days.

(21) Appl. No.: 12/585,692

(22) Filed: Sep. 22, 2009

(65) Prior Publication Data
US 2010/0028926 A1    Feb. 4, 2010

Related U.S. Application Data

(62) Division of application No. 11/660,213, filed as application No. PCT/FR2005/002249 on Sep. 9, 2005, now Pat. No. 7,626,018.

(30) Foreign Application Priority Data

Sep. 10, 2004  (FR) .................................. 04 09593

(51) Int. Cl.
C12Q 1/37     (2006.01)
C07D 265/38   (2006.01)

(52) U.S. Cl. ........... 435/24; 435/34; 435/18; 435/252.1; 435/254.1; 435/255.1; 435/23; 544/101; 544/102

(58) Field of Classification Search .................. 435/24, 435/34, 18, 23, 252.34, 252.2, 254.2, 255.2; 544/101, 102
See application file for complete search history.

(56) References Cited

U.S. PATENT DOCUMENTS

| | | | |
|---|---|---|---|
| 4,259,442 A | 3/1981 | Gayral | |
| 5,336,600 A | 8/1994 | Monget | |
| 6,046,016 A | 4/2000 | Orenga | |
| 6,235,493 B1 | 5/2001 | Bissell et al. | |
| 6,649,365 B1 | 11/2003 | Orenga | |
| 7,420,054 B2 | 9/2008 | James et al. | |
| 2006/0035306 A1 | 2/2006 | James et al. | |
| 2006/0121551 A1 | 6/2006 | James et al. | |

FOREIGN PATENT DOCUMENTS

| | | |
|---|---|---|
| CA | 1322733 | 10/1993 |
| DE | 41 19 956 A1 | 12/1992 |
| DE | 102 51 894 A1 | 5/2004 |
| EP | 0 656 421 A1 | 6/1995 |
| EP | 0 881 284 A1 | 12/1998 |
| EP | 1 293 575 A2 | 3/2003 |
| WO | WO 96/40980 | 12/1996 |
| WO | WO 98/04735 | 2/1998 |
| WO | WO 99/09207 A1 | 2/1999 |
| WO | WO 99/38995 A1 | 8/1999 |
| WO | WO 01/42491 A2 | 6/2001 |
| WO | WO 2004/069804 A1 | 8/2004 |
| WO | WO 2004/101536 A1 | 11/2004 |

OTHER PUBLICATIONS

Stuzka et al. Acta Universitatis Palackinae Olomusensis Facultas Rerum Naturalium (1982) 73(Chem. 21): 69-74.*
A. Agban et al., "Synthesis of New Fluorogenic Substrates Derivated of 7-Amino 4-Trifluoromethylcoumarin. Dectection of Gram-Negative Bacteria Group A Streptococci and Enterococci", Annales Pharmaceutiques Francaises, vol. 48, No. 6, (1990) pp. 326-334, English abstract considered.
J. Nakanishi et al., "Imaging of Conformational Changes of Proteins with a New Environment-Sensitive Flouorescent Probe Designed for Site-Specific Labeling of Recombinant Proteins in Live Cells", Analytical Chemistry, vol. 73, No. 13, (Jul. 1, 2001) pp. 2920-2928.
W. E. Smith, "Formylation of Aromatic Compounds with Hexamethylenetetramine and Trifluoroacetic Acid", J. Org. Chem., vol. 37, No. 24, 4A (1972) pp. 3972-3973.
T. Capecchi et al., "Synthesis of the Bisbenzannelated Spiroketal Core of the γ-Rubromycins. The Use of a Novel Nef-Type Reaction Mediated by Pearlman's Catalyst", J. Chem. Soc., Perkin Trans., vol. 1, (2000) pp. 2681-2688.
T. Motohiro et al., "Fundamental and Clinical Study of Cefpodoxime Proxetil Dry Syrup in the Field of Pediatrics", The Japanese Journal of Antibiotics XLII-7, (Jul. 1989) pp. 2-35b.

* cited by examiner

*Primary Examiner* — Sandra Saucier
*Assistant Examiner* — Susan Hanley
(74) *Attorney, Agent, or Firm* — Oliff & Berridge, PLC

(57) ABSTRACT

Enzymatic phenoxazinone substrates of formula (I):

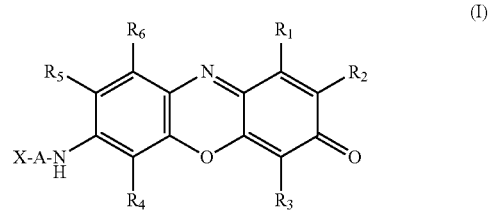

in reaction media containing the same are used for detecting, identifying and/or quantifying microorganisms expressing at least one peptidase activity.

6 Claims, No Drawings

ENZYMATIC SUBSTRATES DERIVED FROM PHENOXAZINONE AND THEIR USE AS DEVELOPERS IN DETECTION OF MICROORGANISMS WITH PEPTIDASE ACTIVITY

This is a Division of application Ser. No. 11/660,213 filed Feb. 15, 2007, now U.S. Pat. No. 7,626,108, which is a National Phase of Application No. PCT/FR2005/002249 filed Sep. 9, 2005, which claims priority to French Patent Application No. 0409593 filed Sep. 10, 2004. The disclosures of the prior applications are hereby incorporated by reference herein in their entireties.

The present invention relates to novel chromogenic enzymatic substrates for the detection of peptidase activity. These substrates can be used in applications comprising an enzymatic hydrolysis step that produces a physicochemical signal, in particular in microbiology, biochemistry, immunology, molecular biology, histology, etc. Compared with the existing substrates, most of which are only fluorigenic, the chromogenic substrates of the invention can be used in particular in a gelled medium for the detection of microorganisms since they produce a coloration that does not diffuse in the reaction medium and is therefore concentrated within the colonies.

The invention also relates to reaction media containing such substrates, to the use of the substrates or the media for detecting Gram-negative bacteria, Gram-positive bacteria and yeasts expressing a peptidase activity, and to methods of use.

An enzyme is generally called an aminopeptidase if it is capable of cleaving by hydrolysis the amide group formed between an acyl of an amino acid and a primary amine, and an enzyme is generally called a peptidase if it is capable of cleaving by hydrolysis the amide group formed between the acyl residue of a peptide and a primary amine. In the present application, the term "peptidase" can denote, as appropriate, both a peptidase and an aminopeptidase as defined above.

Enzymatic chromogenic substrates for the detection of peptidase activity that do not diffuse are described and already known in the prior art. Thus, such substrates are covered by patent applications WO98/04735 and WO99/38995 filed by the applicant. However, these substrates have various drawbacks: they are difficult to synthesize, the purity is low and the yields are low. Furthermore, for use in culture media, a very precise medium composition must be defined in order to observe a color.

The only existing substrates that can be used in solid media for the detection of microorganisms in mixed cultures are acridine-derived substrates and are described in PCT patent application WO2004/069804 filed by the applicant.

Molecules derived from phenoxazinone are known for their ability to produce fluorescence. They can be used:

as acid-base indicators, as described, for example, in Stuzka, V. et al., 1963, Collection Czech. Chem. Commun., 28, 1399-1407, or else as fluorescent labels, for example for following conformation of modifications of proteins, as described in Nakanishi J. et al., 2001, Analytical Chemistry, 73(13), 2920-2928, or else, for example, for the detection of microorganisms as described in U.S. Pat. No. 5,336,600. In the latter case, the compounds described have the drawbacks that they can only be used in liquid media and that the detection of the microorganisms, which occurs via the demonstration of bacterial growth, is carried out by modification of the redox potential. There is therefore no specificity in relation to an enzymatic activity nor in relation to a bacterial genus or species.

No aminophenoxazinone derivative currently described, and in particular no resorufamine derivative, has ever been used as a chromogenic enzymatic substrate that can be used in a gelled medium.

In accordance with the present invention, novel chromogenic enzymatic substrates for detecting microorganisms expressing a peptidase activity are proposed. The invention also relates to reaction media containing such substrates, and also to the use of the substrates or of the media for detecting peptidase activities, and to methods of use.

The applicant has found, surprisingly, that it is possible to detect microorganisms expressing a peptidase activity by using novel chromogenic phenoxazinone derivatives which produce a coloration that does not diffuse in the reaction medium and is therefore concentrated at the colonies, the peptidase activity being demonstrated by a modification of the coloration of the colonies in the culture medium.

After inoculation of the reaction media containing the substrates of the invention, with the microorganisms to be tested, colonies which are colorless-to-white are observed when they are not capable of hydrolyzing the substrate. On the other hand, colored colonies are observed when they are capable of hydrolyzing the substrate of the invention.

The phenoxazinone derivatives of the invention are both chromogenic and fluorigenic and have the advantage of having a good detection sensitivity. In addition, the excitation and the emission of the fluorescence take place in the visible spectrum, such that the fluorescence can be detected by the naked eye and under normal illumination.

Thus, a subject of the present invention is chromogenic enzymatic substrates of formula (I):

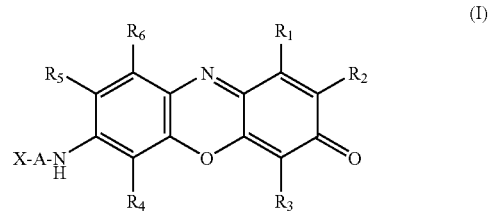

in which $R_1$ represents a hydrogen atom, a $C_1$-$C_{12}$ alkyl group, a $C_6$-$C_{14}$ aralkyl group, an aryl group, —COOH, —COOR$^X$ or —N"R'", $R_2$ represents a hydrogen atom, a halogen atom, a $C_1$-$C_{12}$ alkyl group, —COOH or —COOR', $R_3$ represents a hydrogen atom, a halogen atom, a $C_1$-$C_{12}$ alkyl group, —CN, —CONH$_2$, —COOR' or —COR', $R_4$, $R_5$ and $R_6$ each independently represent a hydrogen atom, a halogen atom, —COOR' or a $C_1$-$C_3$ alkyl group, it being understood that at least one of $R_4$, $R_5$ and $R_6$ is a hydrogen atom, R' represents a hydrogen atom or a $C_1$-$C_6$ alkyl group, R" and R'" each independently represent a $C_1$-$C_6$ alkyl group, or else R" and R'", together with the nitrogen atom to which they are attached, form a heterocyclic ring containing one or more heteroatoms, A represents at least one amino acid, and X represents a blocking agent or nothing.

According to the invention, the term "aryl" is in particular intended to mean a $C_6$-$C_{12}$ aromatic ring, especially phenyl, benzyl, 1-naphthyl or 2-naphthyl. The same is true of the aryl part of the aralkyl groups. Thus, the alkyl group of the $C_6$-$C_{14}$ aralkyl group is $C_2$-$C_8$.

The term "$C_x$-$C_y$ alkyl group" is intended to mean a straight or branched alkyl having from x to y carbon atoms, in the present case from 1 to 12 carbon atoms, from 1 to 6 carbon atoms, or from 1 to 3 carbon atoms or from 2 to 8 carbon atoms. By way of example, mention may be made of methyl, ethyl, propyl, isopropyl, butyl, isobutyl, t-butyl, pentyl, isopentyl, hexyl, heptyl, octyl, nonyl, decyl, undecyl and dodecyl.

The term "halogen atom" is intended to mean chlorine, bromine, iodine or fluorine.

The term "heteroatom" is intended to mean an atom other than a carbon atom, for instance O, N or S.

The heterocyclic rings that R" and R''' can form may be of any size, but they preferably contain from 5 to 7 ring members.

Examples of a heterocyclic ring include the morpholine, piperazine, piperidine, pyrrolidine and imidazolidine rings.

The blocking agents according to the invention include any blocking agent known to those skilled in the art which is capable of protecting amines. By way of example, mention may be made of t-butoxycarbonyl (N-tBOC), 9-fluorenyloxycarbonyl, a solubilizing agent such as succinyl, or else a non-metabolizable, i.e. unnatural, amino acid such as pipecolic acid.

The blocking agents are not systematically present in the compounds of the invention. In this case, i.e. when the compounds of the invention do not have a blocking agent (X is nothing), the compounds of the invention are in the form of a salt such as chloride, bromide or trifluoroacetate.

The amino acids that are represented by A in formula (I) are any amino acid known to those skilled in the art.

According to a specific embodiment, a subject of the present invention is also chromogenic enzymatic substrates of formula (I):

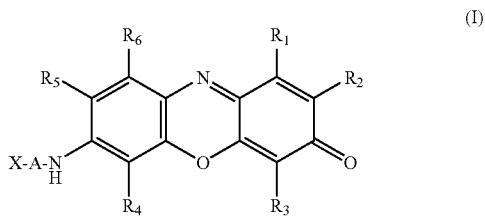

in which $R_1$ represents a hydrogen atom, a $C_1$-$C_{12}$ alkyl group, a $C_6$-$C_{14}$ aralkyl group, an aryl group, —COOH, —COOR' or —NR"R''', $R_2$ represents a hydrogen atom, a halogen atom, a $C_1$-$C_{12}$ alkyl group, —COOH or —COOR', it being understood that at least one of $R_1$ and $R_2$ is a hydrogen atom or a halogen atom, $R_3$ represents a hydrogen atom, a halogen atom, —CN, —CONH$_2$, —COOR' or —COR', $R_4$, $R_5$ and $R_6$ each independently represent a hydrogen atom or a $C_1$-$C_3$ alkyl group, it being understood that at least one of $R_4$, $R_5$ and $R_6$ is a hydrogen atom, R' represents a hydrogen atom or a $C_1$-$C_6$ alkyl group, R" and R''' each independently represent a $C_1$-$C_6$ alkyl group, or else R" and R''', together with the nitrogen atom to which they are attached, form a heterocyclic ring containing one or more heteroatoms, A represents at least one amino acid, and X represents a blocking agent or nothing.

According to one embodiment of the invention, A represents an amino acid or a peptide having at most 10 amino acids, in which the amino acids are identical or different. Preferably, in the interests of cost of the substrate, A represents an amino acid or a peptide having at most 4 amino acids, in which the amino acids are identical or different.

Among the amino acids suitable for the purposes of the invention, mention may, for example, be made of α-alanine and β-alanine, leucine, proline and pyroglutamine.

According to one embodiment of the invention, the compounds of the invention for which $R_1$ represents an alkyl group and $R_2$ represents a hydrogen group are preferred. More preferably, $R_1$ represents a $C_1$-$C_6$, or even $C_3$-$C_6$, alkyl group, methyl and pentyl being particularly preferred.

The compounds for which $R_1$ represents a hydrogen atom and $R_2$ represents a $C_1$-$C_6$ alkyl group constitute another embodiment of the invention. The compounds for which $R_2$ represents an ethyl or hexyl group are preferred.

According to yet another embodiment, the compounds of the invention are such that $R_3$, $R_4$, $R_5$ and $R_6$ each represent a hydrogen atom.

According to another embodiment, the compounds for which $R_1$ and $R_2$ represent an alkyl group or a halogen atom and $R_4$ represents a hydrogen atom, an alkyl group or —COOR', where R' is an alkyl group, are also preferred. Preferred alkyl groups are $C_1$-$C_3$, preferably $C_1$, alkyl groups.

According to another embodiment, the compounds for which $R_1$, $R_2$, $R_3$ and $R_4$ are alkyl groups or a hydrogen atom are also preferred. Alkyl groups that are preferred are $C_1$-$C_3$, preferably $C_1$, alkyl groups.

The compounds of the invention can be prepared according to the procedure represented in scheme 1 below:

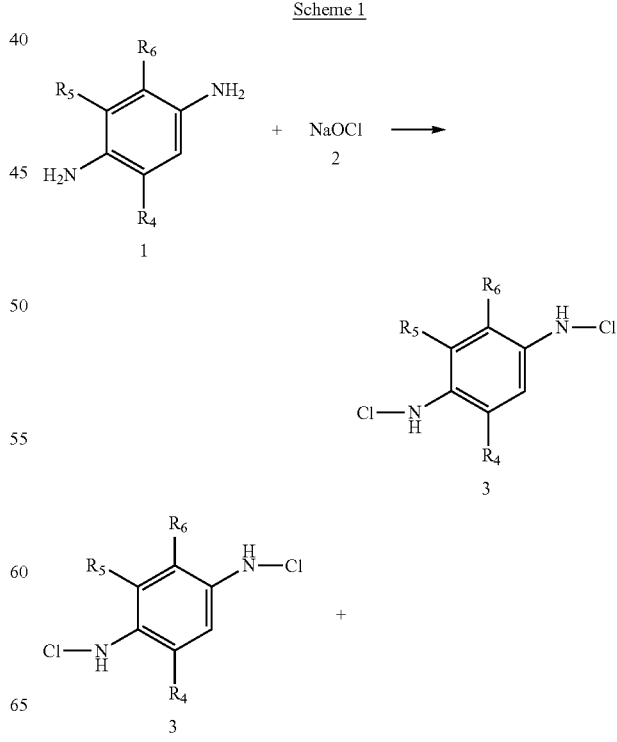

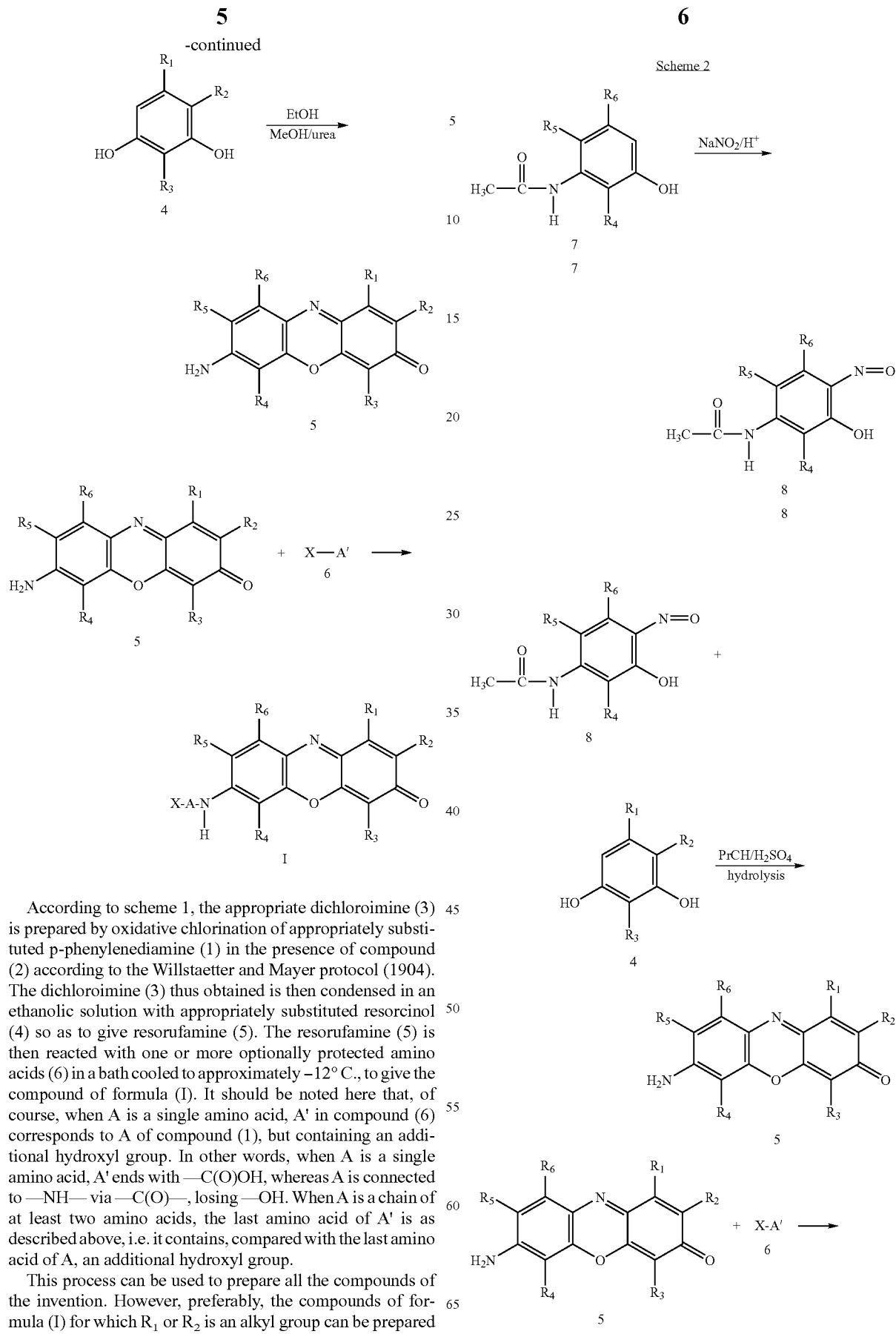

According to scheme 1, the appropriate dichloroimine (3) is prepared by oxidative chlorination of appropriately substituted p-phenylenediamine (1) in the presence of compound (2) according to the Willstaetter and Mayer protocol (1904). The dichloroimine (3) thus obtained is then condensed in an ethanolic solution with appropriately substituted resorcinol (4) so as to give resorufamine (5). The resorufamine (5) is then reacted with one or more optionally protected amino acids (6) in a bath cooled to approximately −12° C., to give the compound of formula (I). It should be noted here that, of course, when A is a single amino acid, A' in compound (6) corresponds to A of compound (1), but containing an additional hydroxyl group. In other words, when A is a single amino acid, A' ends with —C(O)OH, whereas A is connected to —NH— via —C(O)—, losing —OH. When A is a chain of at least two amino acids, the last amino acid of A' is as described above, i.e. it contains, compared with the last amino acid of A, an additional hydroxyl group.

This process can be used to prepare all the compounds of the invention. However, preferably, the compounds of formula (I) for which $R_1$ or $R_2$ is an alkyl group can be prepared according to the protocol described in scheme 2 below.

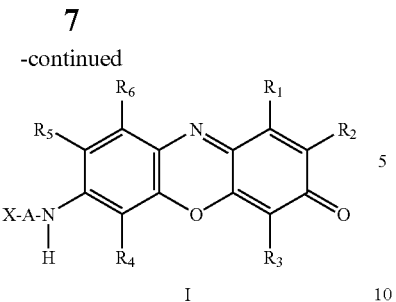

In scheme 2 above, the nitroso compound (8) is prepared by reaction of an appropriately substituted 3-aminophenol (7) with an alkali metal nitrite, such as sodium nitrite, in the presence of phosphoric acid or of sulfuric acid, at a temperature of from 0 to −3° C. The nitrosoacetamidophenol compound (8) thus obtained is then reacted with an appropriately substituted resorcinol (4) in a solvent such as propanol or butanol, in the presence of sulfuric acid as acid catalyst, and a cyclization agent. The acetamidophenoxazinone thus obtained is deacetylated by means of a brief period of heating in the presence of sulfuric acid at 90° C., which process is followed by cooling and by an aqueous precipitation. The resorufamine (5) thus obtained is then reacted with one or more optionally protected amino acids (6) as indicated in the protocol of scheme 1.

The compounds can also be prepared according to the following protocol, as represented in scheme 3:

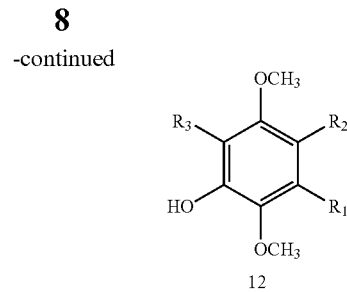

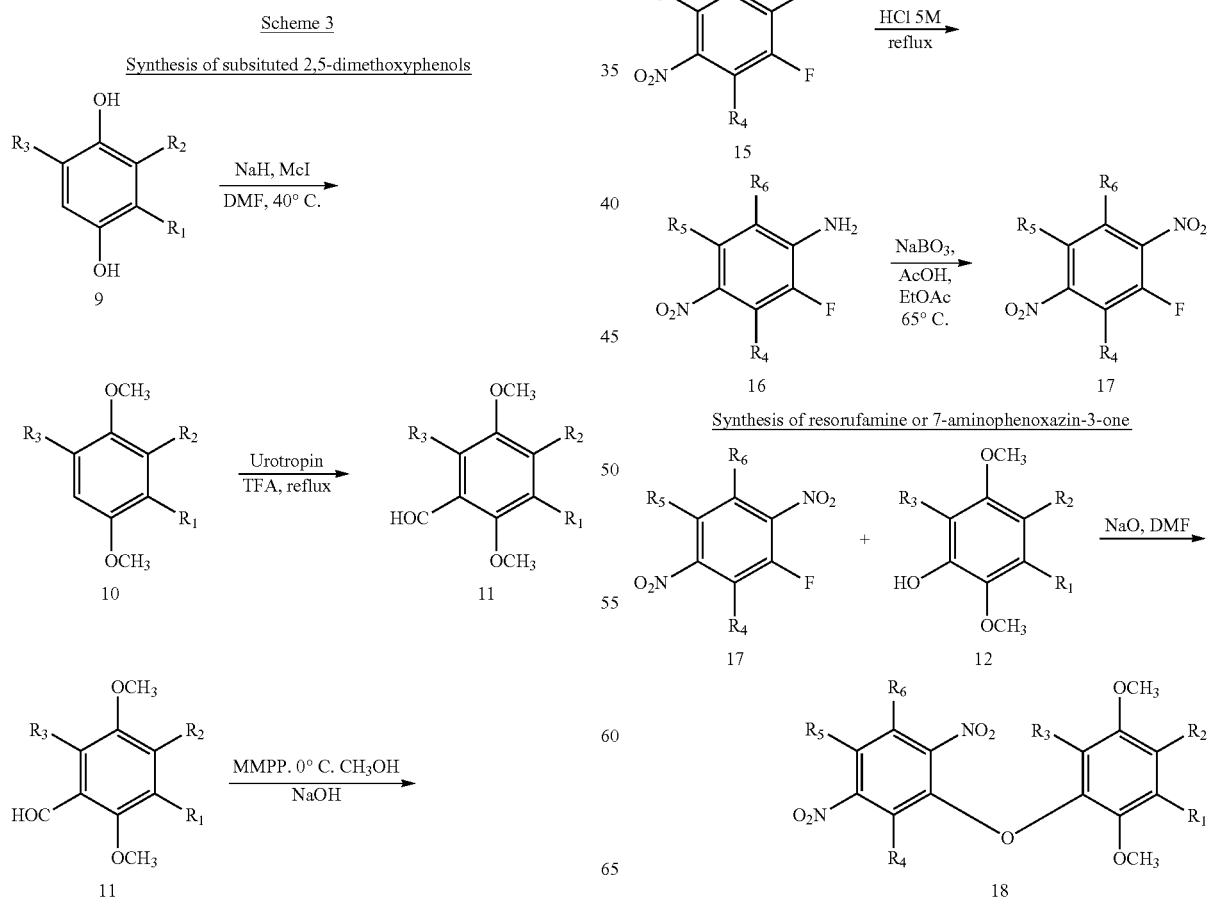

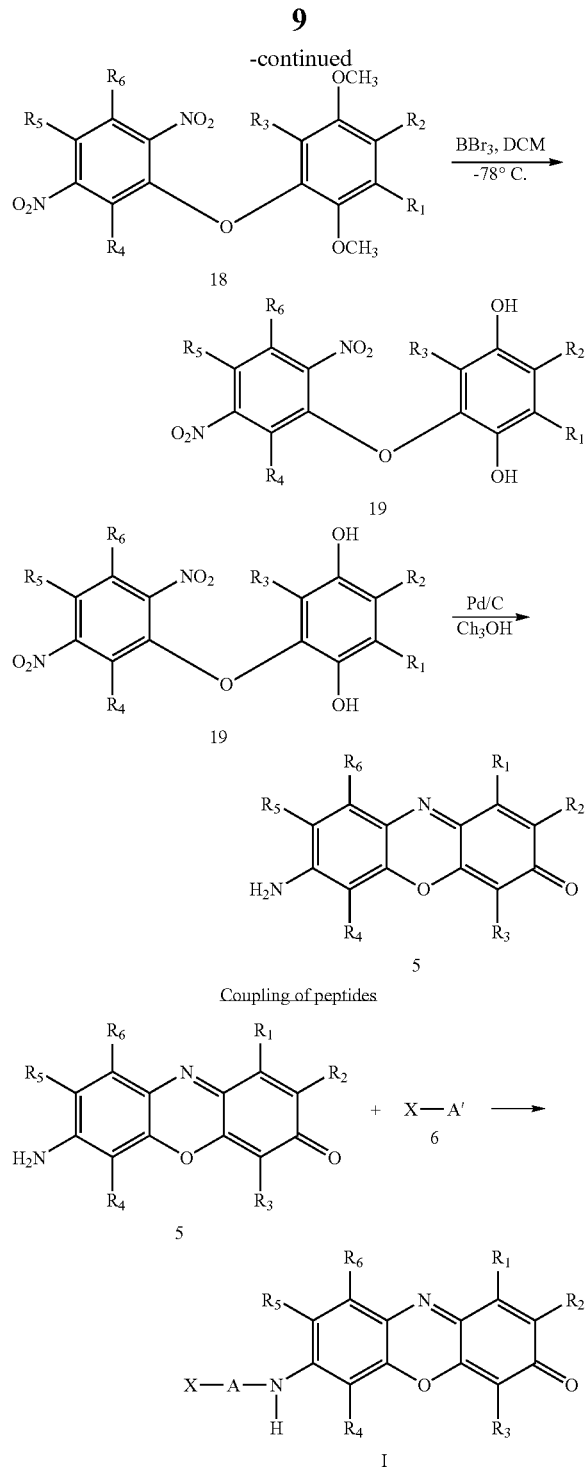

In scheme 3 above, the compounds of the invention are prepared in 4 stages.

According to the first stage, the appropriately substituted 2,5-dimethoxyphenol compound (12) is prepared from a hydroquinone compound (9), also appropriately substituted. This compound (9) is added in dimethylformamide (DMF) with NaH, and then with methyl iodide, which reaction is followed by stirring at 40° C., to give the appropriately substituted 2,5-dimethoxyphenyl compound (10). This compound is then added in trifluoroacetate (TFA) with urotropin under reflux according to the Duff reaction (Smith W E, 1972, J. Org. Chem., 37: 3972), to give the appropriately substituted 2,5-dimethoxybenzaldehyde (11). Finally, compound (11) is added in methanol with magnesium monoperoxyphthalate at 0° C., and then DMF with NaOH according to the Bayer-Villiger reaction (Capecchi T., et al., 2000, J. Chem. Soc., Perkin Trans. 1, 2681), to give the appropriately substituted 2,5-dimethoxyphenol (12).

According to the $2^{nd}$ stage, the 2,5-dinitrofluorobenzene (17) is prepared from an appropriately substituted fluoroaniline (13). This compound (13) is added at 0° C. in triethylamine and dichloromethane (DCM) with acetyl chloride, to give the appropriately substituted N-acetylfluoroaniline (14). This compound is then added with a mixture of concentrated sulfuric acid and of nitric acid in acetic acid, to give the appropriately substituted nitroaniline compound (15). This compound (15) is brought to reflux with hydrochloric acid, to give the nitroaniline compound (16) which is itself added in acetic acid with sodium perborate at 65° C., to give the compound (17).

According to the $3^{rd}$ stage, the resorufamine (5) is obtained by reaction of the 2,5-dimethoxybenzene (12) obtained in the $1^{st}$ stage and of the 2,5-dinitrofluorobenzene (17) obtained in the $2^{nd}$ stage, as follows: compounds (12) and (17) are added in DMF with NaH at ambient temperature, to give the appropriately substituted diaryl ether (18). This compound (18) is then added in DCM with BBr₃, to give the dihydroxydiaryl ether (19) which is itself added to methanol in the presence of the Pd/C catalyst, to give the resorufamine (5).

Finally according to the last stage, the resorufamine (5) thus obtained is then mixed with one or more optionally protected amino acids (6), as indicated in the protocol of scheme 1.

In the above protocols, the starting reactants (compounds (1), (2), (4), (6), (7), (9) and (13)) are commercially available, in particular from Sigma.

A subject of the invention is also a reaction medium comprising at least one chromogenic enzymatic substrate of formula (I) as defined above, alone or in combination with at least one other enzymatic substrate specific for an enzymatic activity other than that detected by the substrate according to the invention.

In fact, when microorganisms expressing a peptidase activity are inoculated into or onto a reaction medium containing the compounds of the invention, a coloration occurs which does not diffuse in or on the reaction medium and is therefore concentrated at the colonies.

According to the invention, the term "reaction medium" is intended to mean a medium that allows the development of at least one enzymatic activity of at least one microorganism.

This reaction medium can either be used only as a developing medium, or as a culture and developing medium. In the first case, the culturing of the microorganisms is carried out before inoculation, and, in the second case, the reaction medium also constitutes the culture medium, and this constitutes a specific embodiment of the invention.

The reaction medium may be solid, semi-solid or liquid. The term "solid medium" is intended to mean, for example, a gelled medium.

Agar is the conventional solid medium in microbiology for culturing microorganisms, but it is possible to use gelatin, agarose or another gelling agent. A certain number of preparations are commercially available, for instance Columbia agar, trypcase-soy agar, MacConkey agar, Sabouraud agar or, more generally, those described in the Handbook of Microbiological Media (CRC Press).

Preferably, when the reaction medium is also a culture medium, it is in gel form.

The amount of agar in the reaction medium is from 2 to 40 g/l. For the solid media, the amount of agar is preferably from 9 to 25 g/l, more preferably from 12 to 14 g/l, and for the semi-solid media, the amount of agar is preferably from 2 to 6 g/l.

The enzymatic substrates of the invention can be used in a wide pH range, in particular between pH 5.5 and 10.

The concentration of enzymatic substrate of the invention in the reaction medium is between 0.01 and 1 g/l, preferably between 0.025 and 0.40 g/l, and it is advantageously 0.05 g/l. This is because, at this substrate concentration, a better coloration contrast is obtained.

The reaction medium may comprise at least one other substrate specific for an enzymatic activity other than that detected by the substrate according to the invention. The enzymatic hydrolysis of the other substrate(s) generates a detectable signal that is different than the signal detected by the substrate of the invention, for instance different colored or fluorescent products, so as to allow the demonstration, such as the detection and/or the identification and/or the quantification, of one or more microorganisms.

By way of other specific substrates, mention may be made of substrates of indoxyl type, such as 5-bromo-4-chloro-3-indoxyl-β-D-glucoside (BIOSYNTH) or 5-bromo-6-chloro-3-indoxyl-β-D-galactoside (BIOSYNTH), or any other substrate used in the detection of microorganisms.

The concentration of the other specific enzymatic substrate is generally between 0.01 and 2 g/l. Those skilled in the art will be able to readily determine such a concentration according to the substrate used.

The reaction medium may also comprise one or more elements in combination, such as amino acids, peptones, carbohydrates, nucleotides, minerals, vitamins, antibiotics, surfactants, buffers, phosphate salts, ammonium salts, sodium salts or metal salts. Examples of media are described in the applicant's patent applications EP 656 421 and WO99/09 207.

The enzymatic substrates and reaction media of the invention can therefore be used in the diagnosis of microorganisms with peptidase activity.

Thus, a subject of the present invention is also the use of a chromogenic enzymatic substrate of formula (I), or of a reaction medium as defined above, for detecting and/or identifying and/or quantifying, in vitro, microorganisms expressing at least one peptidase activity.

The invention also relates to a method for detecting and/or identifying and/or quantifying microorganisms expressing at least one peptidase activity, characterized in that it consists in:
providing a reaction medium, as defined above,
inoculating the medium with a biological sample to be tested,
leaving this to incubate, and
revealing the presence of at least one peptidase activity alone or in combination with at least one other enzymatic activity other than this same peptidase activity.

The inoculation and incubation steps are widely known to those skilled in the art.

For example the incubation temperature is generally between 20 and 55° C., most commonly between 25 and 45° C., temperatures of 30, 35 and 37° C. being the incubation temperatures most commonly used. As regards the incubation atmosphere, it is anaerobic or aerobic without distinction.

The developing is carried out by the naked eye by visualization of a change in coloration that does not diffuse in the reaction medium and is therefore concentrated at the colonies.

By way of microorganisms that can be diagnosed by virtue of the enzymatic substrate of the invention, mention may be made of Gram-negative bacteria, Gram-positive bacteria and yeasts.

By way of Gram-negative bacteria, mention may be made of bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella* and *Legionella*.

By way of Gram-positive bacteria, mention may be made of bacteria of the following genera: *Enterococcus, Streptococcus, Staphylococcus, Bacillus, Listeria, Clostridium, Mycobacteria* and *Corynebacteria*.

Examples of yeasts include yeasts of the following genera: *Candida, Cryptococcus, Saccharomyces* and *Trichosporon*.

The substrates of the invention are particularly suitable for the detection of Gram-negative bacteria because both a microorganism growth and a clear coloration of the colonies are obtained.

In particular, the chromogenic substrates of the invention in which A is L-alanine have the advantage that they make it possible to clearly differentiate Gram-negative bacteria from Gram-positive bacteria.

Thus, another subject of the invention consists of a method for differentiating bacteria in terms of whether they belong to Gram-positive microorganisms or to Gram-negative microorganisms, characterized in that it consists in:
providing a reaction medium, as defined above and in which the substituent A of the chromogenic substrate is L-alanine,
inoculating the medium with a biological sample to be tested,
leaving this to incubate, and
revealing the presence of at least one color variation synonymous with the presence of Gram-negative microorganism(s).

The chromogenic substrates of the invention in which A is β-alanine or pyroglutamine have the advantage that they make it possible to distinguish *Pseudomonas aeruginosa* from the other genera, and also from the other strains of *Pseudomonas*.

Thus, another subject of the invention consists of a method for detecting *Pseudomonas aeruginosa*, characterized in that it consists in:
providing a reaction medium, as defined above and in which the substituent A of the chromogenic substrate is β-alanine or pyroglutamine,
inoculating the medium with a biological sample to be tested,
leaving this to incubate, and
revealing the presence of at least one color variation synonymous with the presence of *Pseudomonas aeruginosa* microorganism(s).

The biological samples to be analyzed are any clinical sample, such as a saliva, blood, urine or stool specimen or any other sample of which the analysis may aid a clinician in providing a diagnosis. The sample may also be a product derived from, or a base product of, the food and/or pharmaceutical industry, in which it is necessary either to guarantee the absence of pathogenic microorganisms, or to count a contaminating flora, or to detect specific microorganisms.

The invention will be understood more fully from the following examples, given by way of nonlimiting illustration.

EXAMPLE 1

Synthesis of 7-N—(N'-t-butoxycarbonyl-L-alanyl)amino-2-chloro-1-pentylphenoxazin-3-one and of 7-N—(N'-t-butoxycarbonyl-L-alanyl)-amino-1-pentylphenoxazin-3-one 1,4-Dichlorobenzoquinonediimine was prepared by chlorination of 1.76 g (10 mmol) of p-phenylenediamine, and was dissolved by heating in the presence of anhydrous methanol (50 ml) and 9 g of urea added to the stirred solution. 1.8 g (10 mmol) of 5-pentylresorcinol was subsequently added to the solution at 40-50° C. and, after complete dissolution, the reaction mixture was brought to reflux carefully in order to avoid excessive exothermia. The heating was continued for 1.5 h, after which time the cooled reaction mixture was added slowly to a well-stirred ice/water mixture containing ammonia. The precipitate was recovered by suction filtration and was washed with water and then air dried so as to obtain 2.2 g of crude product consisting of a mixture of the title compounds, the non-chlorinated product being predominant.

Acetic acid (30%, 200 cm$^3$) from a 2-necked flask was added, dropwise, while stirring, to a solution consisting of approximately 5 g of sodium borohydride and 200 mg of sodium hydroxide dissolved in 200 cm$^3$ of water. Hydrogen gas was passed through a 3-necked flask in which the mixture of 7-amino-2-chloro-1-pentylphenoxazin-3-one and 7-amino-1-pentylphenoxazin-3-one (0.564 g) was dissolved in anhydrous dimethylformamide (15 cm$^3$ by heating and then cooling) and the solution was diluted with anhydrous tetrahydrofuran (THF) (15 cm$^3$). A Pd/C catalyst (5%, 200 mg) was added to the solution. The solution was sparged gently with hydrogen gas and this was continued for a long time after the apparent reduction (approximately 1 h). The reduction was demonstrated by the solution turning from a purple color to a grayish-green color. A solution of resorufamine was thus obtained.

In a separate flask, 0.756 g (4.0 mmol) of N-t-Boc-L-alanine and 0.408 g (4.0 mmol) of N-methylmorpholine were dissolved in anhydrous THF (10 cm$^3$), the solution was cooled to −20° C. and 0.56 cm$^3$ (4.0 mmol) of isobutyl chloroformate was added, with stirring. The mixture was stirred at −20° C. for a further 30 min, after which time the mixture was introduced, at −10° C., into the solution of resorufamine with stirring, while at the same time sparging with hydrogen gas. After 15 min, the introduction of hydrogen was stopped, the system was sealed and the reaction mixture was stirred overnight at ambient temperature. The reaction mixture was filtered and the solvent was evaporated off under reduced pressure, the residual solid was dissolved in dichloromethane (DCM), the DCM solution was filtered and washed with NaHCO$_3$ (5%, twice 50 cm$^3$) and water (50 cm$^3$). The organic phase was dried with MgSO$_4$, filtered and concentrated so as to obtain a residue consisting of the two title products. They were purified by silica column chromatography, elution being carried out with a mixture of petrol and ethyl acetate (7:3). The first spot corresponds to 7-N—(N'-t-butoxycarbonyl-L-alanyl)amino-2-chloro-1-pentyl-phenoxazin-3-one in the form of an orange solid and the second spot corresponds to 7-N—(N'-t-butoxycarbonyl-L-alanyl)-amino-1-pentylphenoxazin-3-one in the form of a brown solid.

EXAMPLE 2

Synthesis of 7-N—(N'-t-butoxycarbonyl-D-alanyl)amino-2-chloro-1-pentylphenoxazin-3-one and of 7-N—(N'-t-butoxycarbonyl-D-alanyl)-amino-1-pentylphenoxazin-3-one The protocol described in example 1 above was repeated, except that N-t-Boc-β-alanine was used in place of N-t-Boc-L-alanine.

In order to recover the title compounds, silica column chromatography was performed, elution being carried out with a mixture of petrol/ethyl acetate (6:4). The first spot corresponds to 7-N—(N'-t-butoxycarbonyl-β-alanyl)amino-2-chloro-1-pentylphenoxazin-3-one in the form of an orange solid and the second spot corresponds to 7-N—(N'-t-butoxycarbonyl-p-alanyl)-amino-1-pentylphenoxazin-3-one in the form of an orange solid.

EXAMPLE 3

Deprotection of the Aminated Derivatives

To do this, the compounds obtained in examples 1 and 2 were dissolved in 2 cm$^3$ of TFA (trifluoroacetate) in the following proportions: 0.10 g (0.21 mmol) for the 7-N—(N'-t-butoxycarbonyl-L-alanyl)amino-2-chloro-1-pentylphenoxazin-3-one and 80 mg (0.18 mmol) each for the 7-N—(N'-t-butoxycarbonyl-L-alanyl)amino-1-pentylphenoxazin-3-one, 7-N—(N'-t-butoxycarbonyl-β-alanyl)amino-2-chloro-1-pentyl-phenoxazin-3-one and 7-N—(N'-t-butoxycarbonyl-β-alanyl)amino-1-pentylphenoxazin-3-one.

The mixture was kept at ambient temperature for 15 min. The progression of the reaction was recorded by thin layer chromatography until no further starting material was demonstrated. The TFA was evacuated off under vacuum and the residue was completely washed with ether and dried so as to obtain the various compounds in the form of a trifluoroacetate salt (brown solid), according to the following yields: 0.095 g (92%) for the 7-N—(N'-t-butoxycarbonyl-L-alanyl)amino-2-chloro-1-pentylphenoxazin-3-one and 80 mg (97%) each for the 7-N—(N'-t-butoxycarbonyl-L-alanyl)amino-1-pentylphenoxazin-3-one, 7-N—(N'-t-butoxycarbonyl-p-alanyl)amino-2-chloro-1-pentylphenoxazin-3-one and 7-N—(N'-t-butoxycarbonyl-β-alanyl)amino-1-pentylphenoxazin-3-one.

EXAMPLE 4

Synthesis of 7-N-(L-pyroglutamyl)amino-2-chloro-1-pentyl-phenoxazin-3-one and 7-N-(L-pyroglutamyl)amino-1-pentylphenoxazin-3-one The protocol described in example 1 above was repeated, except that 0.516 g of L-pyroglutamic acid was used in place of the N-t-Boc-L-alanine.

In order to recover the title compounds, silica column chromatography was performed, elution being carried out with a mixture of DCM/MeOH (95:5). The first spot corresponds to 7-N-(L-pyroglutamyl)amino-2-chloro-1-pentylphenoxazin-3-one in the form of a brown solid and the second spot corresponds to 7-N-(L-pyroglutamyl)-amino-1-pentylphenoxazin-3-one in the form of a brown solid.

EXAMPLE 5

Synthesis of 7-N—(N'-t-butoxycarbonyl-O-alanyl)amino-1,2-dimethyl-phenoxazin-3-one and of 7-N—(N'-t-butoxycarbonyl-β-alanyl)amino-1,2,4-trimethyl-phenoxazin-3-one

5.1. General Procedure for the Preparation of Dimethoxybenzenes

In a dry round-bottomed, 2-necked flask equipped with a condenser, with a magnetic stirrer bar and with a calcium chloride protection tube, hydroquinone (1 molar equivalent) was dissolved in 50 ml of anhydrous dimethylformamide (DMF) and 2.2 molar equivalents of NaH were added in small amounts. After addition of the base and when the $H_2$ had stopped evolving, 4 molar equivalents of methyl iodide were added dropwise in 15-20 min. Once the addition was complete, the reaction mixture was stirred at 40° C. for 2 hours. 200 ml of salt water was added to the flask and the resulting mixture was extracted with diethyl ether (3 times 50 ml). The combined organic layers were washed with water (twice 50 ml) and the product was dried over $MgSO_4$. The solvent was evaporated off under reduced pressure and the residue was subjected to column chromatography.

5.1.1 1,4-Dimethoxy-2,3-dimethylbenzene

The process was carried out as described in point 5.1 above, using 1.957 g (0.01416 mol) of 2,3-dimethylhydroquinone. The product was isolated in the form of a white solid (2.27 g, 80%) using a 95:5 mixture of light mineral spirit:diethyl ether.

5.1.2. 1,4-Dimethoxy-2,3,5-trimethylbenzene

The process was carried out as described in point 5.1 above, using 2.175 g (0.01429 mol) of 2,3,5-trimethylhydroquinone. The product was isolated in the form of a colorless oil (2.367 g, 92%).

5.2. Formylation of Dimethoxybenzenes by Means of the Duff Reaction 1 equivalent of dimethoxybenzene was dissolved in 20 ml of TFA and 1.05 equivalents or urotropin were added to the resulting solution. The reaction mixture was brought to reflux for 2 hours under anhydrous conditions. The TFA was evaporated off under reduced pressure, the residue was dissolved in 100 ml of ether and the organic solution was washed with water (3 times 50 ml) and then dried over $MgSO_4$. The solvent was evaporated off and the residue was subjected to column chromatography, elution being carried out with an 80:20 mixture of light mineral spirit (60-80° C.):diethyl ether.

5.2.1. 2,5-Dimethoxy-3,4-dimethylbenzaldehyde

The process was carried out as described in point 5.2 above, using 2.270 g (0.01366 mol) of 1,4-dimethoxy-2,3-dimethylbenzene. The title product was isolated in the form of a white solid (1.18 g, 44%).

5.2.2 2,5-Dimethoxy-3,4,6-trimethylbenzaldehyde

The process was carried out as described in point 5.2 above, using 2.274 g (0.01262 mol) of 1,4-dimethoxy-2,3,5-trimethylbenzene. The title product was isolated in the form of a yellow solid (1.21 g, 46%).

5.3 General Procedure for the Preparation of Phenols Using Bayer-Villiger Oxidation 0.033 mol of dimethoxybenzaldehyde was dissolved in 50 ml of methanol and a suspension of magnesium monoperoxyphthalate (MMPP) (0.018 mol) in 50 ml of methanol was added dropwise while keeping the reaction mixture at 0° C. Once the addition was complete, the reaction mixture was stirred at ambient temperature for 4 hours. The resulting ester was hydrolyzed under basic conditions using 50 ml of 1M NaOH. After 1 hour, three quarters of the methanol was removed under reduced pressure, the excess base was neutralized with 1M HCl and the pH was adjusted to 3. The phenol was extracted in ethyl acetate (3 times 50 ml), the combined organic layers were dried over $MgSO_4$, the solvent was evaporated off and the residue was subjected to column chromatography.

5.3.1. 2,5-Dimethoxy-3,4-dimethylphenol

The process was carried out as described in point 5.3 above, using 1.126 g (5.797 mmol) of 2,5-dimethoxy-3,4-dimethylbenzaldehyde. The title product was isolated in the form of a yellow oil (0.239 g, 23%) using, as eluent, a 60:40 mixture of light mineral spirit (60-80° C.):diethyl ether.

5.3.2. 2,5-Dimethoxy-3,4,6-trimethylphenol

The process was carried out as described in point 5.3 above, using 1.205 g (5.786 mmol) of 2,5-dimethoxy-3,4,6-dimethylbenzaldehyde. The title product was isolated in the form of a white solid (0.856 g, 75%) using, as eluent, a 75:25 mixture of light mineral spirit (60-80° C.):diethyl ether.

5.4. General Procedure for Preparing Diaryl Ethers 1 molar equivalent of appropriate phenol was dissolved in 10 ml of anhydrous DMF and 1.1 molar equivalents of NaH were added in small amounts. After complete development of the gas, the resulting sodium phenolate solution was stirred at ambient temperature for 15 minutes. 1 molar equivalent of a solution of 2,5-dinitrofluorobenzene in 5 ml of anhydrous THF was added dropwise to the flask and the reaction mixture was stirred for 2 hours. At the end, the content of the flask was poured into 50 ml of water, the mixture was extracted with ether (3 times 50 ml) and the combined organic layers were dried over MgSO4. The solvent was removed under reduced pressure and the residue was subjected to column chromatography.

5.4.1 1-(2',5'-Dinitrophenoxy)-3,4-dimethylbenzene

The process was carried out as described in point 5.4 above, using 0.293 g (1.575 mmol) of 2,5-dinitrofluorobenzene and 0.287 g (1.575 mmol) of 2,5-dimethoxy-3,4-dimethylphenol. The title product was obtained in the form of an orange solid (0.415 g, 76%) after column chromatography using, as eluent, an 85:15 mixture of light mineral spirit (60-80° C.):ethyl acetate.

5.4.2 1-(2',5'-dinitrophenoxy)-3,4,6-trimethylbenzene

The process was carried out as described in point 5.4 above, using 0.812 g (4.362 mmol) of 2,5-dinitrofluorobenzene and 0.856 g (4.362 mmol) of 2,5-dimethoxy-3,4,6-trimethylphenol. The title product was obtained in the form of a yellow solid (1.412 g, 89%) after column chromatography using, as eluent, a 75:25 mixture of light mineral spirit (60-80° C.):diethyl ether.

5.5. General Procedure for Deprotecting Hydroquinone Methyl Ethers 1 molar equivalent of dimethyl aryl ether was dissolved in 30 ml of anhydrous DCM and the mixture was cooled to −78° C. 2.5 molar equivalents of $BBr_3$ in hexane (1 M) were added dropwise to the cooled solution of ether and the reaction product was stirred at −78° C. for 30 min. The mixture was then heated to ambient temperature and stirred until the end of the reaction (followed by thin layer chromatography). The reaction mixture was diluted with 10 ml of methanol at 0° C. and was poured into 50 ml of water. The organic layer was separated and the aqueous layer was washed with ethyl acetate (3 times 25 ml). The combined organic layers were dried over $MgSO_4$. The solvent was removed and the residue was subjected to column chromatography.

5.5.1. 1-(2',5'-Dinitrophenoxy)-3,4-dimethyl-2,5-dihydroxybenzene

The title compound was not isolated, but it was formed and then reduced and cyclized directly according to a reaction in the same container (see point 5.6.1. below).

5.5.2. 1-(2',5'-Dinitrophenoxy)-3,4,6-trimethyl-2,5-dihydroxybenzene

The process was carried out as described in point 5.5 above, using 0.626 g (1.728 mmol) of 1-(2',5'-dinitrophenoxy)-2,5-dimethoxy-3,4,6-dimethylbenzaldehyde. The title product was isolated in the form of an orange solid (0.435 g, 75%) using, as eluent, a 70:30 mixture of light mineral spirit (60-80° C.):diethyl ether.

5.6. General Procedure for Preparing 7-aminophenoxazin-3-ones 1.3 mmol of dihydroxydiaryl ether were dissolved in 5 ml of methanol and Pd/C 5% catalyst (10% weight/weight) was added to the solution. The reaction mixture was stirred at ambient temperature in the hydrogenation apparatus under a hydrogen atmosphere for 4 hours. Silica was added to the flask (in sufficient amount in view of the residue load to be introduced into the column chromatography) and the mixture was vigorously stirred for a further 4 hours with free access to the air. At the end of the oxidation, the solvent was removed and the residue was subjected to column chromatography using an eluent gradient, starting from a 50:50 mixture of light mineral spirit (60-80° C.):ethyl acetate, then changing to a 25:75 mixture then a 0:100 mixture of the same solvents. Finally, a 90:10 mixture of ethyl acetate:methanol was used as eluent.

5.6.1. 7-Amino-1,2-dimethylphenoxazin-3-one

The process was carried out as described in point 5.6 above, starting from 0.266 g (0.7636 mmol) of 1-(2',5'-dinitrophenoxy)-3,4-dimethyl-2,5-dihydroxybenzene, according to a reaction in the same container. The title product was obtained in the form of a reddish-brown solid (0.125 g, 68%).

5.6.2. 7-Amino-1,2,4-trimethylphenoxazin-3-one

The process was carried out as in point 5.6 above, starting from 0.435 g (1.3013 mmol) of 1-(2',5'-dinitrophenoxy)-3,4,6-trimethyl-2,5-dihydroxybenzene. The title product was obtained in the form of a reddish-brown solid (0.237 g, 72%).

5.7 General Procedure for Coupling a Peptide to the 7-aminophenoxazin-3-ones 0.4 mmol of 7-aminophenoxazin-3-one was dissolved in 5 ml of anhydrous DMF in a small round-bottomed flask containing a magnetic stirrer bar, and 0.010 g of $Pd/C_5$% catalyst was added to the solution. The flask was placed in a hydrogenation apparatus at ambient temperature and a hydrogen atmosphere was maintained while stirring the reaction mixture for 1 hour. It was possible to confirm complete reduction by virtue of the fact that the solution changed color from deep purple to grayish-green. In a separate flask, 0.089 g (0.4719 mmol) of N-t-Boc-alanine, 0.072 g (0.4719 mmol) of hydroxybenzotriazole (HOBt) and 0.07 ml (0.4719 mmol) of diisopropylcarbodiimide (DIC) were dissolved in 5 ml of anhydrous DCM and the reaction mixture was stirred at ambient temperature for 1 hour. After this period, the content of the second flask was introduced into the first flask (which contained the reduced form of the 7-aminophenoxazin-3-one) by means of a syringe under an inert atmosphere. The presence of oxygen from the air was avoided due to the very rapid oxidation of the reactant. The mixture was stirred for a further 20 hours at ambient temperature. The reaction mixture was filtered through celite and the solvent was evaporated off. The residue was redissolved in 20 ml of ethyl acetate, and the organic layer was washed with 20 ml of 1M HCl, 20 ml of 10% $Na_2CO_3$ and 20 ml of water. The product was dried over $MgSO_4$, filtered, and evaporated under reduced pressure so as to obtain a residue that was purified by column chromatography using a 30:70 mixture of light mineral spirit (60-80° C.):ethyl acetate as eluent.

5.7.1 7-N—(N'-t-Butoxycarbonyl-β-alanyl)amino-1,2-dimethylphenoxazin-3-one

The process was carried out as described in point 5.7. above, using 0.110 g (0.4578 mmol) of 7-amino-1,2-dimethylphenoxazin-3-one. The title product was obtained in the form of a reddish-brown solid (0.104 g, 55%).

5.7.2 7-N—(N'-t-Butoxycarbonyl-β-alanyl)amino-1,2,4-trimethylphenoxazin-3-one The process was carried out as described in point 5.7. above, using 0.100 g (0.3933 mmol) of 7-amino-1,2,4-trimethylphenoxazin-3-one. The title product was obtained in the form of an orange solid (0.113 g, 68%).

5.8. Deprotection of the N-t-butoxycarbonyl Group 0.2 mmol of the corresponding N-t-butoxycarbonyl-protected compound was dissolved in 3 ml of anhydrous DCM and 1 ml of TFA was added to the solution. The reaction mixture was stirred at ambient temperature until the end of the reaction (followed by thin layer chromatography). The solvent and the excess TFA were evaporated off under reduced pressure and the residue was purified by short column chromatography using an eluent gradient, starting from a 50:50 mixture of light mineral spirit (60-80° C.):ethyl acetate, then changing to a 0:100 mixture of the same solvents. Finally, a 90:10 mixture of ethyl acetate:methanol was used as eluent.

5.8.1. 7-N-(β-Alanyl)amino-1,2-dimethylphenoxazin-3-one trifluoroacetate salt The process was carried out as indicated in point 5.8. above, using 0.047 g (0.1138 mmol) of 7-N—(N'-t-butoxycarbonyl-β-alanyl)amino-1,2-dimethylphenoxazin-3-one. The title product was obtained in the form of a red solid (0.046 g, 95%).

5.8.2. 7-N-(β-Alanyl)amino-1,2,4-trimethylphenoxazin-3-one trifluoroacetate salt The process was carried out as indicated in point 5.8. above, using 0.081 g (0.1897 mmol) of 7-N—(N'-t-butoxycarbonyl-β-alanyl)amino-1,2,4-trimethylphenoxazin-3-one. The title product was obtained in the form of a red solid (0.080 g, 96%).

EXAMPLE 6

Preparation of methyl 7-N—(N'-t-butoxycarbonyl-β-alanyl)amino-1-methyl-2-chlorophenoxazin-3-one-4-carboxylate 1.76 g (10 mmol) of 1,4-dichlorobenzoquinoneimine were dissolved in 50 ml of absolute ethanol with gentle stirring. 1.82 g (10 mmol) of methyl 4-methyl-2,6-dihydroxybenzoate were added to this stirred solution. The stirred solution was gently refluxed until the point where a considerable exothermia became apparent, requiring the flask to be removed from the heat source. After the exothermia had decreased, the reaction mixture was brought to reflux for a further 30 minutes and allowed to cool to ambient temperature. After having left the reaction mixture at ambient temperature for a further 3 hours, the solid product was recovered by suction filtration and washed with a small amount of hot water followed by suctioning so as to obtain it in as dry a state as possible, before drying in a desiccator under vacuum. The residue was subjected to silica gel thin layer chromatography with ethyl acetate as the mobile phase. A considerable amount of dark-colored base product and also the fluorescent pink component were observed. The solid product was dissolved in ethyl acetate, filtered and passed through a silica gel cone. The filtrate is essentially devoid of base product. The solvent was removed under reduced pressure and the solid product was isolated.

The solid product was subjected to an aminoacylation using t-BOC-O-alanine, as described above, so as to obtain the title compound.

EXAMPLE 7

Synthesis of 7-N—(N'-t-butoxycarbonyl-O-alanyl)amino-6-methyl-phenoxazin-3-one

7.1. Synthesis of N-acetyl-2-methyl-3-fluoroaniline 1.98 ml (27.78 mmol) of acetyl chloride were added, with stirring, to a solution of 3.161 g (25.26 mmol of 2-methyl-3-fluoroaniline and 3.87 ml (27.78 mmol) of triethylamine in 50 ml of DCM at 0° C. The solution was allowed to warm up to ambient temperature and was stirred for 1 hour. The solution was washed with water (3 times 50 ml), the product was dried with MgSO$_4$ and the solvent was removed under reduced pressure. After recrystallization from a mixture of mineral oil/ethyl acetate (EtOAc), 3.844 g (91%) of the title compound were obtained in the form of white crystals.

7.2. Synthesis of N-acetyl-2-methyl-3-fluoro-4-nitroaniline

The compound obtained in point 7.1 above was reacted with a mixture of 5 ml of concentrated sulfuric acid and of 5 ml of nitric acid in 10 ml of acetic acid at 18° C. for 1 hour. The reaction solution was subsequently diluted in 100 ml of water and was extracted in ethyl acetate (EtOAc) (3 times 50 ml), and dried over MgSO$_4$ and the solvent was removed under vacuum. The title compound was isolated in the form of a white solid (1.96 g, 71%).

7.3. Synthesis of 2-methyl-3-fluoro-4-nitroaniline 1.311 g (6.18 mmol) of the compound obtained in point 7.2. above were brought to reflux in 5M hydrochloric acid for 2 hours. The solution was neutralized with sodium carbonate and was then extracted with diethyl ether (3 times 50 ml) and dried over MgSO$_4$, and the solvent was removed under vacuum. The residue was purified by column chromatography using a 70:30 mixture of mineral spirit:EtOAc as eluent. The title product was isolated in the form of a yellow solid (0.589 g, 94%).

7.4. Synthesis of 2-fluoro-3,6-dinitrotoluene

A solution of 0.357 g (2.10 mmol) of the compound obtained in point 7.3. above in 4 ml of acetic acid was added, dropwise, to a solution of 1.61 g (10.46 mmol) of sodium perborate tetrahydrate in 11 ml of EtOAc, at 65° C., and the mixture was stirred for 6 hours. The reaction solution was diluted in 50 ml of water and the mixture was extracted in diethyl ether (3 times 20 ml) and dried over MgSO$_4$, and the solvent was removed under vacuum. The residue was purified by column chromatography using a 70:30 mixture of mineral spirit:trichloromethane as eluent, so as to obtain the title product in the form of a yellow liquid (0.274 g, 65%).

7.5 Synthesis of 2,5-dimethoxyphenol

The process was carried out as indicated in point 5.3. above, using 5.53 g (0.0333 mol) of 2,5-dimethoxybenzaldehyde. The title product was isolated in the form of a yellow oil, using an 80:20 mixture of light mineral spirit (60-80° C.):diethyl ether as eluent (4.27 g, 83%).

7.6 Synthesis of 1-(3',6'-dinitro-2'-methylphenoxy)-2,5-dimethoxybenzene

The process was carried out as indicated in point 5.4. above, using 0.366 g (1.83 mmol) of the 2-fluoro-3,6-dinitrotoluene prepared in point 7.4. above and 0.282 g (1.83 mmol) of 2,5-dimethoxyphenol prepared in point 7.5. above. The title product was isolated in the form of a yellow solid, using a 70:30 mixture of light mineral spirit (60-80° C.):diethyl ether as eluent (0.400 g, 65.5%).

7.7. Synthesis of the Title Compound

The title compound can be obtained as indicated in points 5.5. to 5.7. above.

EXAMPLE 8

Detection of the L-Alanine Peptidase Activity of Gram-Negative Bacteria

The compounds, chlorinated or nonchlorinated, prepared in example 1, i.e. 7-N—(N'-t-butoxycarbonyl-L-alanyl) amino-2-chloro-1-pentylphenoxazin-3-one (chlorinated L-alanyl compound) and 7-N—(N''-t-butoxycarbonyl-L-alanyl)amino-1-pentylphenoxazin-3-one (nonchlorinated L-alanyl compound), which were deprotected according to the protocol described in example 3, were used.

10 mg of each of the L-alanyl compounds were dissolved in 1 ml of dimethylsulfoxide, and the mixture was added to 200 ml of molten Columbia agar at 50° C. The medium thus constituted was dispensed into Petri dishes (final concentration of each substrate: 50 mg/l).

Strains from international collections or derived from the applicant's collection were then inoculated, using a 10 μl calibrated loop, onto each medium, using calibrated suspensions of 0.5 McFarland. All the strains were also inoculated onto Columbia agar media without chromogenic substrate, as a growth control. All the cultures were incubated for 24 to 48 h at 37° C.

The growth and coloration results obtained between 24 and 48 h of incubation are given in table 1, in which G signifies growth, C signifies color, I signifies colorless, the sign ++ signifies very good growth, the sign + signifies good growth of the strain, the sign +/− signifies average growth of the strain and the sign − signifies absence of growth of the strain.

TABLE 1

| No. | Strain name | International accession No. | Nonchlorinated L-alanyl compound | | Chlorinated L-alanyl compound | | Control |
|---|---|---|---|---|---|---|---|
| | | | G | C | G | C | C |
| 1 | Escherichia coli | NCTC 10418 | purple | + | pink/purple | + | + |
| 2 | Klebsiella pneumoniae | NCTC 10896 | purple | + | pink/purple | + | + |
| 3 | Salmonella hadar | | purple | + | pinl/purple | + | + |
| 4 | Proteus mirabilis | NCTC 10975 | purple | + | pink/purple | + | + |
| 5 | Staphylococcus aureus | NCTC 6571 | I | − | I | + | + |
| 6 | Providencia rettgeri | NCTC 7475 | purple | + | pink/purple | + | + |
| 7 | Pseudomonas aeruginosa | NCTC 10662 | purple | + | pink/purple | + | ++ |
| 8 | Listeria monocytogenes | NCTC 11994 | I | − | I | + | + |
| 9 | Streptococcus pyogenes | NCTC 8306 | I | − | I | +/− | +/− |

The results in table 1 above show that the enzymatic substrate of the invention makes it possible to detect all the bacterial strains since they all grow, but a modification of coloration is observed only for the Gram− strains (strains 1 to 4 and 6 to 7), which also makes it possible to discriminate between the Gram− strains and the Gram+ strains.

EXAMPLE 9

Detection of the β-alanine Peptidase Activity of Bacteria of the *Pseudomonas aeruginosa* Genus To do this, the chlorinated or nonchlorinated β-alanine compounds prepared in example 2, i.e. 7-N—(N'-t-butoxycarbonyl-β-alanyl)amino-2-chloro-1-pentylphenoxazin-3-one (chlorinated beta-alanyl compound) and 7-N—(N'-t-butoxycarbonyl-β-alanyl)amino-1-pentylphenoxazin-3-one (nonchlorinated beta-alanyl compound), which were deprotected according to the protocol described in example 5, were used.

In addition, the Petri dishes were prepared and the strains were inoculated according to the protocol described in example 5.

The coloration results between 24 and 48 h of incubation are indicated in table 2 below.

TABLE 2

| Strain name | International accession No. | Nonchlorinated beta-alanyl compound | Chlorinated beta-alanyl compound |
|---|---|---|---|
| Pseudomonas aeruginosa | | purple | purple |
| Pseudomonas aeruginosa | | purple | pale purple |
| Pseudomonas aeruginosa | | purple | pale purple |
| Pseudomonas aeruginosa | | purple | purple |
| Burkholderia cepacia GI | LMG1222 | yellow | yellow |
| Burkholderia cepacia GIII | LMG 18832 | yellow | yellow |
| Acinetobacter baumannii | ATCC 19606 | colorless | colorless |
| Acinetobacter calcoaceticus | | colorless | colorless |

TABLE 2-continued

| Strain name | International accession No. | Nonchlorinated beta-alanyl compound | Chlorinated beta-alanyl compound |
|---|---|---|---|
| Pseudomonas fragilis | NCIMB 8987 | colorless | colorless |
| Pseudomonas maltophilia | | colorless | colorless |
| Ralstonia basilensis | | colorless | colorless |
| Ralstonia taiwanensis | | colorless | colorless |

The results in table 2 above demonstrate that the compounds of the invention make it possible to preferentially detect *Pseudomonas aeruginosa* bacteria (development of a pale purple to purple coloration).

EXAMPLE 10

Detection of Pyroglutamyl Peptidase Activity

To do this, the chlorinated or nonchlorinated pyroglutamyl compounds prepared in example 4, i.e. 7-N-(L-pyroglutamyl)amino-2-chloro-1-pentylphenoxazin-3-one (chlorinated L-pyroglutamyl compound) and 7-N-(L-pyroglutamyl)amino-1-pentylphenoxazin-3-one (nonchlorinated L-pyroglutamyl compound), which were deprotected according to the protocol described in example 5, were used.

In addition, the Petri dishes were prepared and the strains were inoculated according to the protocol described in example 5.

The coloration results between 24 and 48 h of incubation are indicated in table 3 below.

TABLE 3

| Strain name | International accession No. | Nonchlorinated pyroglutamyl compound | Chlorinated pyroglutamyl compound |
|---|---|---|---|
| Pseudomonas aeruginosa | | purple | purple |
| Pseudomonas aeruginosa | | purple | purple |
| Pseudomonas aeruginosa | | purple | purple |
| Burkholderia cepacia GI | LMG1222 | yellow | yellow |
| Burkholderia cepacia GIII | LMG 18832 | yellow | yellow |
| Acinetobacter baumannii | ATCC 19606 | colorless | colorless |
| Acinetobacter calcoaceticus | | colorless | colorless |
| Pseudomonas fluorescens | | colorless | colorless |
| Pseudomonas fragilis | NCIMB 8987 | colorless | colorless |
| Pseudomonas maltophilia | | colorless | colorless |
| Ralstonia basilensis | | colorless | colorless |
| Ralstonia taiwanensis | | colorless | colorless |

The results in table 3 above demonstrate that the compounds of the invention make it possible to preferentially detect *Pseudomonas aeruginosa* bacteria.

EXAMPLE 11

Detection of the β-alanine Peptidase Activity of Bacteria of the *Pseudomonas aeruginosa* Genus To do this, the β-alanine compounds prepared in examples 5 and 6, i.e. 7-N—(N'-t-butoxycarbonyl-β-alanyl)amino-1,2-dimethylphenoxazin-3-one (b-ala-DMP), 7-N—(N'-t-butoxycarbonyl-β-alanyl)amino-1,2,4-trimethylphenoxazin-3-one (b-ala-TMP) and 7-N—(N'-t-butoxycarbonyl-β-alanyl)amino-1-methyl-2-chloro-4-(oxo-1-methyl)phenoxazin-3-one (b-ala-MCMP), which were deprotected as described in the previous examples, were used.

In addition, the Petri dishes were prepared and the strains were inoculated according to the protocol described in example 7. The coloration results between 24 and 48 h of incubation are indicated in table 4 below.

TABLE 4

| Strain name | International accession No. | b-ala-DMP | b-ala-TMP | b-ala-MCMP |
|---|---|---|---|---|
| Pseudomonas aeruginosa | ATCC 10145 | deep pink | orangy-pink | violet |
| Pseudomonas aeruginosa | ATCC 27853 | pink | pink | violet |
| Pseudomonas aeruginosa | * | deep pink | orangy-pink | violet |
| Pseudomonas aeruginosa | ATCC 9027 | deep pink | pink | pink-violet |
| Pseudomonas aeruginosa | * | colorless | colorless | colorless |
| Pseudomonas fluorescens | * | colorless | colorless | colorless |
| Pseudomonas putida | * | colorless | colorless | colorless |
| Burkholderia cepacia | LMG 18941 | pale pink | pale pink | colorless |
| Burkholderia Gladioli | LGM 6880 | colorless | colorless | colorless |
| Escherichia coli | * | orange | orange | colorless |

* Applicant's collection

The results in table 4 above demonstrate that the compounds of the invention make it possible to preferentially detect *Pseudomonas aeruginosa* bacteria (development of a pink-to-violet coloration). It may also be noted that the results can vary in terms of color and color strength, just as they can in terms of sensitivity and specificity in relation to the *Pseudomonas aeruginosa* species, according to the substituents used and their position on the main ring, such that the use of these various substrates can be envisioned in different specific applications depending on the intended objective.

What is claimed is:

1. A reaction medium comprising at least one chromogenic peptidase substrate according to formula (I) below, alone or in combination with at least one other enzymatic substrate specific for an enzymatic activity other than that detected by said peptidase substrate:

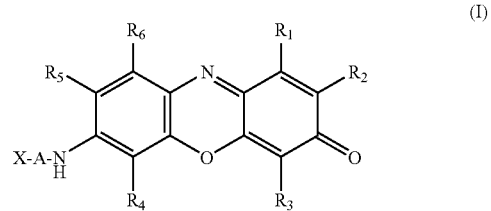

(I)

wherein:
R1 represents a hydrogen atom, a C1-C12 alkyl group, a C6-C14 aralkyl group, an aryl group, —COOH, —COOR' or —NR"R'",
R2 represents a hydrogen atom, a halogen atom, a C1-C12 alkyl group, —COOH or —COOR',
R3 represents a hydrogen atom, a halogen atom, a C1-C12 alkyl group, —CN, —CONH2, —COOR' or —COR',
R4, R5 and R6 each independently represent a hydrogen atom, a halogen atom, —COOR' or a C1-C3 alkyl group, at least one of R4, R5 and R6 is a hydrogen atom,
R' represents a hydrogen atom or a C1-C6 alkyl group, R" and R'" each independently represent a C1-C6 alkyl group, or R" and R'", together with the nitrogen atom to which they are attached, form a heterocyclic ring containing one or more heteroatoms, A represents at least one amino acid residue, and X represents a blocking moiety or is not present.

2. The reaction medium of claim 1, wherein the reaction medium is a culture medium.

3. The reaction medium of claim 1, wherein the reaction medium is in a gelled form.

4. A method for detecting and/or identifying and/or quantifying microorganisms expressing at least one peptidase activity in a biological sample, the method comprising:

providing a reaction medium as defined in claim 1, inoculating the reaction medium with a biological sample to be tested to provide an inoculated reaction medium, incubating the inoculated reaction medium, and detecting and/or identifying and/or quantifying the microorganisms expressing at least one peptidase activity by observing color in the incubated inoculated medium wherein said peptidase activity is observed alone or in combination with at least one other enzymatic activity other than said peptidase activity.

5. A method for determining if a biological sample comprises Gram-positive microorganisms or Gram-negative microorganisms, the method comprising:

providing a reaction medium as defined in claim 1 and in which the substituent A of the chromogenic substrate is an L-alanine residue, inoculating the reaction medium with a biological sample to be tested to provide an inoculated reaction medium, incubating the inoculated reaction medium, and observing the development of color in the incubated inoculated reaction medium wherein the development of color indicates the presence of the Gram-negative microorganisms.

6. A method for detecting *Pseudomonas aeruginosa* in a biological sample, the method comprising:

providing a reaction medium as defined in claim 1 and in which the substituent A of the chromogenic substrate is a beta-alanine residue or a pyroglutamine residue, inoculating the reaction medium with a biological sample to be tested to provide an inoculated reaction medium, incubating the inoculated reaction medium, and observing a coloration of the incubated inoculated reaction medium which indicates the presence of *Pseudomonas aeruginosa*.

* * * * *